US010973698B2

(12) United States Patent
Lipshaw et al.

(10) Patent No.: US 10,973,698 B2
(45) Date of Patent: Apr. 13, 2021

(54) GARMENT FOR A HAND (71) Applicant: MEDI USA, L.P., Whitsett, NC (US)

(72) Inventors: Moses Lipshaw, Encinitas, CA (US);
Karen Lynch, San Diego, CA (US);
Kevin Larmer, San Diego, CA (US);
Ingrid Adams, San Diego, CA (US);
Thomas Richardson, San Diego, CA (US)

(73) Assignee: MEDI USA, L.P., Whitsett, NC (US)

( * ) Notice: Subject to any disclaimer, the term of this patent is extended or adjusted under 35 U.S.C. 154(b) by 465 days.

(21) Appl. No.: 15/615,191

(22) Filed: Jun. 6, 2017

(65) Prior Publication Data

US 2017/0354544 A1 Dec. 14, 2017

Related U.S. Application Data

(60) Provisional application No. 62/347,536, filed on Jun. 8, 2016.

(51) Int. Cl.
| A61F 13/06 | (2006.01) |
| A61F 13/10 | (2006.01) |
| A61F 5/01 | (2006.01) |
| A61F 13/08 | (2006.01) |
| A61F 5/32 | (2006.01) |
| A61F 5/34 | (2006.01) |

(52) U.S. Cl.
CPC .......... *A61F 13/104* (2013.01); *A61F 5/0118* (2013.01); *A61F 5/32* (2013.01); *A61F 5/34* (2013.01); *A61F 13/085* (2013.01); *A61F 13/10* (2013.01)

(58) Field of Classification Search
CPC ...... A61F 13/104; A61F 13/10; A61F 5/0118; A61F 5/0104; A61F 5/013; A61F 5/01; A61F 5/05866; A61F 5/05858; A61F 5/05841; A61F 13/107; A61F 13/108; A61F 13/00; A61F 13/00004; A61F 13/00021; A61F 5/00; A61F 13/08; A61F 13/085
See application file for complete search history.

(56) References Cited

U.S. PATENT DOCUMENTS

| 4,047,250 A | * | 9/1977 | Norman ............... A41D 13/088 2/161.1 |
| 4,632,105 A | | 12/1986 | Balow |
| 5,451,201 A | * | 9/1995 | Prengler ................. A61F 5/012 602/13 |
| 5,755,679 A | | 5/1998 | Selner et al. |

(Continued)

FOREIGN PATENT DOCUMENTS

| ES | 2242682 T3 | 11/2005 |
| WO | 01/08618 A1 | 2/2001 |

*Primary Examiner* — Victoria J Hicks
(74) *Attorney, Agent, or Firm* — Rimôn, P.C.

(57) ABSTRACT

A compression garment for a hand. The garment includes a body portion dimensioned to wrap at least partially around a hand of a user and includes a trimmable portion. An aperture of the body portion is disposed opposite the trimmable portion wherein the aperture is configured for receiving a thumb of the user. A plurality of bands are extended from an edge of the body portion in communication with the trimmable portion. Each band can be trimmable to a plurality of sizes (e.g. length, width, or the like) and can include a proximal end connected to the body portion and a distal free end having a fastener.

19 Claims, 8 Drawing Sheets

(56) References Cited

U.S. PATENT DOCUMENTS

| | | | |
|---|---|---|---|
| 6,338,723 B1* | 1/2002 | Carpenter | A61F 13/069 602/60 |
| 9,642,559 B2* | 5/2017 | Falconio-West | A61B 5/6828 |
| 2004/0106889 A1* | 6/2004 | Robinson | A61F 5/0118 602/64 |
| 2007/0191747 A1 | 8/2007 | Daneshvar | |
| 2008/0287848 A1* | 11/2008 | Jaccard | A61F 5/0118 602/21 |
| 2010/0312160 A1* | 12/2010 | Creighton | A61L 15/42 602/62 |
| 2011/0087145 A1* | 4/2011 | Farrow | A61F 5/0118 602/22 |
| 2011/0125183 A1* | 5/2011 | Lipshaw | A61F 13/085 606/201 |
| 2013/0319128 A1* | 12/2013 | Richardson | A61F 13/08 73/818 |
| 2016/0058623 A1 | 3/2016 | Lipshaw et al. | |

\* cited by examiner

GARMENT FOR A HAND

CROSS REFERENCE TO RELATED APPLICATIONS

This present application claims priority to U.S. Provisional Patent Application No. 62/347,536, entitled "Garment for a hand", filed Jun. 8, 2016, wherein the entire application is incorporated by reference herein in its entirety

FIELD

Compression garments for the treatment of circulatory disorders such as Lymphedema.

BACKGROUND

Lymphedema is swelling that occurs when excessive protein-rich lymph fluid accumulates in the interstitial tissue. This lymph fluid may contain plasma proteins, extravascular blood cells, excess water, and parenchymal products. Lymphedema is one of the most poorly understood, relatively underestimated, and least researched complications of common diseases like cancer, and thus the prevalence of lymphedema within the general population is largely unknown. Nevertheless, for those who are diagnosed with lymphedema, the standard of care consists of meticulous skin care, manual lymphatic drainage, exercise therapy, inelastic compression bandaging and, eventually, compression garments.

The frequency and duration of care is dependent on individual subject's therapeutic need and may range from 2 to 3 visits per week for 6 or more weeks depending on the severity of lymphedema and any other associated impairment.

The use of compression bandaging, although proven effective in reducing edema, has its drawbacks. The application of inelastic compression bandages is time consuming and requires a skilled clinician. Furthermore, because subjects are not easily able to effectively bandage themselves, this treatment strategy does not promote self-care, does not provide sustained therapeutic levels of compression, and requires the subject to frequently return for follow up visits. Lastly, wearing bandages negatively impacts the subject's quality of life with regard to comfort and hygiene which can reduce compliance.

Many bandage alternative wrap type garments exist on the market. These garments are primarily used after the intensive phase treatment of lymphedema to maintain the patient's limb size. Most of the wrap garments lack the ability to adapt to changes in limb size and are cost prohibitive to be used as a short term bandage replacement in the intensive phase. For those garments that are available the sizing adjustments can be complex and time consuming for practical use. The embodiments of the present disclosure address these and other related needs in the art.

SUMMARY

In some embodiments, a compression garment for a hand is disclosed. The garment can include a body portion dimensioned to wrap at least partially around the hand. An aperture of the body portion can be included for receiving a thumb of the hand (e.g. by being slid, inserted, or otherwise positioned through the aperture). A plurality of bands may be extended from an edge of the body portion. The edge can be opposite the aperture. Each band can be operable to securely wrap around the hand between a plurality of tensions. Each band can include a proximal end connected (e.g. fixedly connected, detachably connected, or integrally formed therewith) to the body portion and a distal end that comprises a fastener. The distal end can also be trimmable. The body portion can be trimmable about the proximal ends of the bands to a plurality of dimensions to fit the hand and wrist areas.

In some embodiments, the garment is reversible and configured for use with both a right hand and a left hand. In this respect, the user would simply flip the garment and it could be used with either hand.

In some embodiments, the garment can also include indicia on the body portion indicating the distance between the aperture and the edge of the body portion the plurality of bands extends.

In some embodiments, the garment can include indicia on the body portion adjacent the proximal end of the bands, each indicia corresponding to a different dimension of the hand (e.g. palm circumference, hand circumference, palm width, etc.). The indicia may be spaced at predetermined intervals, the indicia being ticks, notches, printed dots, shapes, symbols, patterns, and/or text. The indicia can also be curved to guide trimming to conform to a curvature of the hand, such as the palm or other feature of the hand.

In some embodiments, the fastener of each band is a fastener tab detachably connected to the distal end for releasable attachment onto itself and/or onto body portion. Each fastener tab can be removably attached to the body portion and/or the bands causing the respective band to move between one of a plurality of different positions and orientations.

In some embodiments, the aperture is disposed at a position of the body portion between the bands. The aperture can also be trimmable to one of a plurality of different thumb sizes. Indicia can also be disposed on or about the aperture corresponding to the plurality of different thumb sizes.

In some embodiments, the body portion can include an upper edge, a lower edge and a lateral edge opposite the bands and adjacent or near the aperture. The body portion can also be trimmable about the upper edge, the lower edge, and/or the lateral edge. In some embodiments, the upper edge and/or the lower edge can be curved to conform to the size and/or curvature of the hand.

In some embodiments, the plurality of bands can consist of an upper band and a lower band. The upper band can be disposed along an upper edge of the body portion for wrapping between the thumb and onto fingers of the hand. The lower band can be disposed along a lower edge of the body portion for wrapping around the hand below the thumb and onto the arm. A width of the upper band and/or the lower band can be trimmable to reduce coverage over the fingers and arm. Other portions of the upper and/or lower band may also be trimmable.

In some embodiments, a compression and/or tension level measuring system can be included in the body portion and/or one or more of the bands for indicating an actual tension and/or compression level delivered to the hand by the garment. One measuring system can include indicia one or more of the bands and/or the body portion when the garment is donned by the hand with a card. The card can include a scale for measuring a separation of at least one indicia to determine an actual compression level to the hand associated with the separation. The distal end of the bands can be releasably attachable to a plurality of locations and/or orientations so that a respective band can be adjustable between a plurality of compression levels according to the actual compression level measured by the card. In this embodiment, the indicia may be spaced along at predetermined intervals.

Another measuring system can include a multi-layer compression measuring system formed on one or more of the bands and/or the outer surface of the body portion. A stretchable base layer can be included in one or more of the bands and/or the body portion along with an upper layer attached at two spaced-apart locations on top of the stretchable base layer. A visual indicator of the actual compression level can be positioned with the upper or base layers and can be observable when the upper layer is pulled taut. The visual indicator of this system may be indicia on the stretchable base layer such that each of the two spaced-apart locations is adjustable and opposing ends of the upper layer can be aligned with indicia on the stretchable base layer. The upper layer can be rigidly attached to the stretchable base layer at one of the two spaced-apart locations and can be releasably attached to the stretchable base layer at the other of the two spaced-apart locations. The visual indicator of this system may also include three-dimensional arrangements of the particular feature. For example, if the multi-layer system is installed on the first tensioning band, if the upper layer of the system is pulled flat or otherwise arranged, this can indicate a pre-determined compression level.

In some embodiments, the body portion can include a fastener tab detachably connected on the body portion. For example, the fastener tab can be connected on the upper or lower surface of the body portion. In this respect, the fastener tab can be configured to secure the lateral edge about the palm of the hand, wherein the lateral edge can be opposite the edge of the body portion opposite the aperture.

In some embodiments, the body portion can include a lateral edge adjacent the aperture and opposite the edge of the body portion opposite the aperture, the lateral edge being smaller than the edge opposite the aperture. For example, the body portion can be tapered or in conical shape between the respective edges. In other embodiments, the indicia on the bands can relate to other dimensions of the hand, such as the palm and/or wrist circumference.

In some embodiments, a compression garment for a hand is disclosed having a body portion dimensioned to wrap at least partially around a hand of a user. The body portion can include a trimmable portion as well as an aperture. The aperture can be disposed opposite the trimmable portion and be configured for slidably receiving a thumb of the user. A plurality of bands can be extended from an edge of the body portion in communication with the trimmable portion. Each band can be trimmable to a plurality of sizes and include a proximal end connected to the body portion and a distal free end with a fastener.

In some embodiments, a compression garment for a hand is disclosed having a body portion dimensioned to wrap at least partially around a hand of a user. An aperture of the body portion can be included for slidably receiving a thumb of the user. A plurality of bands can also be included that extend from an edge of the body portion opposite the aperture. Each band can include a proximal end connected to the body portion and a distal free end comprising a fastener. Each band being trimmable to a plurality of sizes (e.g. length, width, or some combination thereof can be trimmable). In this regard, a distance between the aperture and the edge of the body portion opposite the aperture can be adjusted by trimming the body portion between the bands. Indicia can be included on the body portion associated with different distances between the aperture and the edge of the body portion opposite the aperture. Each indicia can correspond to a different palm circumference and/or hand size.

In other embodiments, a method of using a compression garment is disclosed. One step can include forming a hand compression garment in accordance with this disclosure. Another step can include trimming the body portion (e.g. trimming the trimmable portion of the body portion) so the body portion is fit to the user's hand. This can include causing the body portion to become smaller and converting the remaining, untrimmed portions into bands thereby customizing the garment to the hand of the user. Trimming can be conducted between the bands on the side of the body portion that is opposite the aperture. In a third step, the thumb can be passed through the aperture of the garment thereby anchoring and selectively positioning the hand with the garment during application. The body portion may then be wrapped around the dorsum of the hand. The method can also include trimming the bands have to one or more desired dimensions. Another step can including positioning the fastener tab of the body portion to be securely engage with the opposing edge of the body portion and/or proximal end of the bands. The fastener tab can be positioned opposite the bands on the body portion and preferably disposed in the central palm. Securing the fastener tab and wrapping the edges together as described can cause a base level of compression over the dorsum of the hand where most hand swelling occurs. In another step, a distal free end of each band can be individually positioned and/or oriented to a location on the body portion, the other band, or itself for a desired tension and thus the targeted compression and location for the hand.

The method can also include measuring the predetermined compression level with any of the herein disclosed measuring systems, for example, by measuring separation of indicia of the first tensioning band and/or the body portion when the tensioning band is tensioned with a card, the card comprising a scale for measuring separation and correlating the separation to a measured compression level; and adjusting the predetermined compression level by repositioning at least one end of the first tensioning band onto the body portion according to the measured compression level.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

DETAILED DESCRIPTION

Unless defined otherwise, all terms of art, notations and other scientific terms or terminology used herein have the same meaning as is commonly understood by one of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "subject" is not limited to a specific species. For example, the term "subject" may refer to a patient, and frequently a human patient. However, this term is not limited to humans and thus encompasses a variety of mammalian species.

Compression therapy is considered the mainstay of treatment for lymphedema which relies on the application of external force in order to increase the internal pressure of the affected limb. Almost any portion of the body can suffer from swelling. However, hand swelling poses a significant challenge due to the variance in size and shape. When hand swelling needs treatment several methods have been used for applying the external force.

A first approach has included bandaging. This typically involves a therapist wrapping the patient's hand, and sometimes fingers, in order to apply the desired level of compression. The bandages are then left in place for as long as possible. While effective, this approach requires a degree of skill and training that is not available to everyone. As a result, individuals who are unable to treat and bandage themselves are often required to leave bandages applied by trained professionals in place for extended periods of time. This often leads to hygiene concerns and is significantly inconvenient.

A second approach has included compression gloves. Compression gloves can also be used to apply therapeutic compression. They can be knit, sewn, made custom to the user's measurements, standard sized, and be composed from a variety of elastic and inelastic materials. While also effective, these gloves typically fall short when swelling reduction is needed and are primarily used for maintenance once swelling has been reduced. Due to the intended use of the products, they are tight fitting by nature which often translates into fit issues and can be challenging to don. Custom gloves made to the patient's measurements can help resolve some of the fit complications. However, even those have issues and can be prohibitively expensive.

A third approach has included hand wraps. This approach typically involves a body portion paired with one or more bands or straps that are used to apply compression. Hand wraps provide a reasonable alternative to bandaging as they enable the user to wrap their hand more easily without training or a special skill set. However, unlike bandages, there is less flexibility with sizing. A bandage can be used to fit almost any hand regardless of shape and size, while hand wraps are more size specific.

Known hand wrap garments and glove options also suffer from delay and reduced treatment time. For example, the patient needs to be measured prior to determining the product size, and then the patient is required to order or find a dealer location where they can purchase the product. This can take weeks which delays treatment and may waste one of the set number of therapy sessions allotted by the insurance companies.

The herein disclosed garment resolves these and other problems of the art. By effectively contouring the intricate shape of the human hand to provide therapeutic compression, by trimming away one or more areas of excess material. The garment can include a trimmable portion that permits the wrap to more effectively contour the shape of the hand and enables the user to customize the body portion of the wrap in accordance with the certain dimensions of the hand (e.g., palm circumference) and then customize the bands (e.g., length, width, etc.) in order to further optimize the fit and therapeutic compression. This novel solution will permit end-users, including medical professionals and therapists, to have one product on a hand that can fit any patient without having to measure the hand to determine product size. This enables end-users to start treatment immediately, similar to bandaging. However, unlike bandaging, hand wraps simplify self-management, which allows the patient to adjust the wrap as swelling reduction is achieved thus improving results. The herein disclosed garment also allows the patient to easily remove and reapply their garment which promotes better hygiene.

Figure 1:
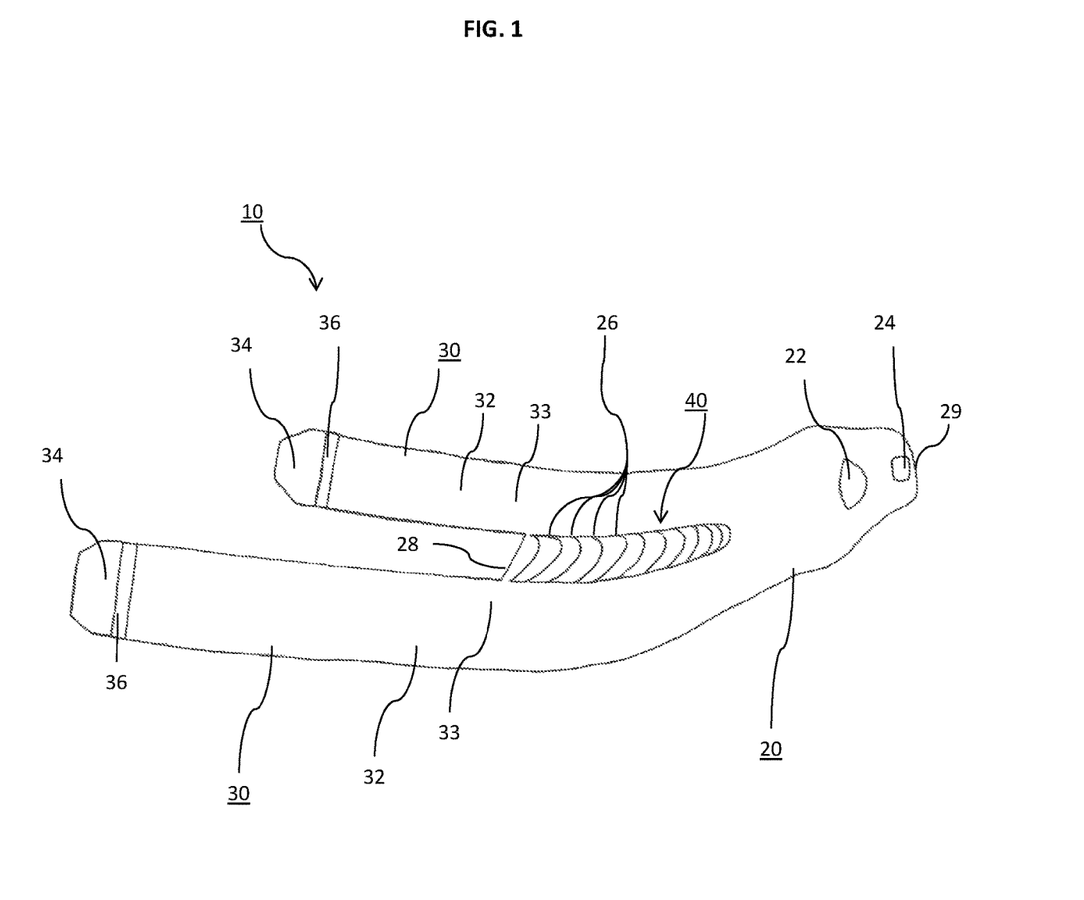
FIG. 1 depicts one exemplary embodiment of a compression garment for a hand.

As can be seen, FIG. 1 shows an uncut exemplary garment 10 laid out flat. The garment 10 can include a body portion 20 with a plurality of band portions 30 extended therefrom. The body portion 20 can be dimensioned to wrap at least partially around the hand of a user, as shown and described more particularly below. An aperture 22 can be included in the body portion 20 can be included for slidably receiving a thumb of the hand. For example, to use the garment, a user may position their thumb through aperture 22 to then secure body portion 20 around the palm and then secure the bands 32 of band portion 30. While two bands 32 are depicted in FIG. 1, any number of bands 32 can be used as need or required.

As depicted, bands 32 may be extended from an edge 28 of the body portion 20 hat is opposite the aperture 22. Aperture 22 could be a hole, a cut out portion, a slit or the like. In those embodiments where aperture 22 could be a slit, the slit could have a hook fastener to adjust size by abutting edges or overlap. Each band 32 can be operable to securely wrap around certain portions of the hand (e.g. the palm, below the thumb, between the thumb and the other fingers, etc.) and can be adjusted between a plurality of tensions. Band 32 can include a proximal end 33 connected (e.g. fixedly connected, detachably connected, or integrally formed therewith) to the body portion and a distal end 34.

The distal end 34 and corresponding portion of band 32 can be trimmable as to its length but also its width. End 34 can also include a detachable fastener (e.g. a fastener tab). This is advantageous as it can permit the band 32 to be trimmable as to width, length, and/or the like for added customization to the specific user and post-trimming the detachable fastener can then be re-positioned on end 34.

As also depicted in FIG. 1, the body portion 20 can also include a trimmable portion 40 that can be disposed between bands 32 and defined between edge 28 and the remainder of the body portion 20. In this respect, the body portion 20 of garment 10 can also be trimmable about or between bands 32 at proximal ends 33 of the bands. This is particularly advantageous as it allows the garment 10 to be easily adjust between one of a plurality of palm circumferences. Trimmable portion 40 can include indicia 26 on the body portion 20 adjacent the proximal end 33 of the bands 32. The indicia 26 can be disposed along a central region of the body portion 20 and the indicia 26 can reference dimensions of the hand (e.g., palm circumference) so as to indicate where the body portion 20 should be trimmed. The indicia 26 can be disposed between the aperture 22 and edge 28 and can be spaced apart. Each interval of indicia 26 can correspond to a different palm circumferences or hand sizes. Indicia 26 can also be one or more ticks, notches, printed dots, shapes, symbols, patterns, and/or text. The indicia 26 can also be curved to guide construction to conform to a curvature of the palm or other feature of the hand. A distance between the aperture 22 and the edge 28 can be adjusted by trimming the trimmable portion of the body portion 20 between the bands 32. Trimming the indicia 26 as disclosed can cause the body portion 20 and garment 10 to fit any sized hand.

The indicia 26 can also simply indicate sizes (e.g. small, medium, large, etc.), whereby the user could simply measure their hand and then compare the measurement to a chart before trimming the trimmable portion 40. While the relevant dimension can be the palm circumference, the herein disclosed garment 10 is not so limited the garment 10 can instead be sized as to palm width, distance from wrist to one or more fingers, or any other dimension. In other embodiments, it is contemplated that the user can trim the trimmable portion 40 down until proper fit is attained without taking any measurements. For example, the body portion 20 could be initially wrapped until the edge 28 is in communication with indicia 26 to determine where to trim. Once determined, the body portion 20 can be trimmed at indicia 26.

In certain embodiments, body portion 20 can be trimmable about its upper edge, lower edge, and/or the lateral edge 29 opposite edge 28. The garment 10 in certain embodiments may be configured for use only with the right hand or only with the left hand. However, garment 10 is not so limited and may instead be reversible and configured for use with both a right hand and a left hand. In this respect, the user would simply flip the garment 10 and insert the thumb through aperture 22 so the garment 10 could be used with either hand. The body 20 and band 30 portions may be constructed from any combination of elastic material, non-elastic material, and/or limited stretch material. The material may also include a UBL surface on one or both sides. In this respect, a dual sided UBL surface on the body 20 and band 30 portions can permit the garment 10 to be reversible and work for both the right and left hand.

The body portion 20 can include a fastener tab 24 detachably connected on the upper or lower surface of the body portion 20. As shown, the fastener tab 24 can be a double-sided fastener and configured to secure the lateral edge 29 about the palm of the hand and towards opposite edge 28. The body portion 20 may include indicia or an indicated engagement area onto which the fastener tab 24 can be positioned. The fastener tab 24 as shown in FIG. 1 is not so limited, however, and may be positioned anywhere on the body portion 20, including the upper surface as depicted or the lower surface (in those embodiments where garment 10 is reversible). Fastener tab 24 may also be closer to edge 28 or closer to the upper or lower edges of the body portion 20. Lateral edge 29 can being smaller than the edge opposite the aperture. For example, the body portion 20 can be tapered or in conical shape between edges 28 and 29. Indicia may also be applied to the body portion 20 to guide placement of the fastener.

Figure 2:
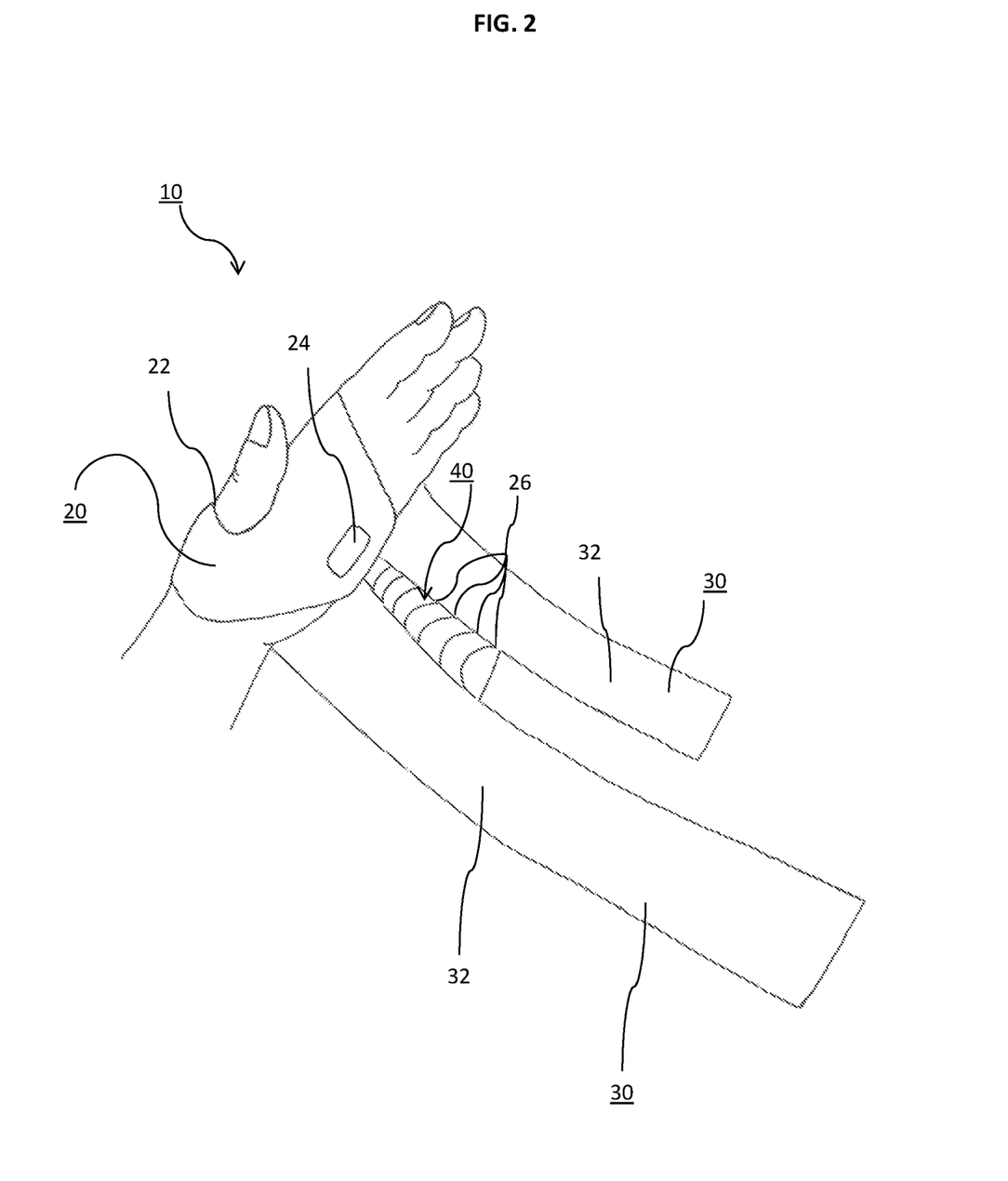
FIG. 2 depicts another exemplary embodiment of the garment of FIG. 1 whereby the garment is being donned and the thumb is shown placed through an aperture.

A method 200 is also disclosed, wherein in step 205, a hand compression garment is formed in accordance with this disclosure, the garment including a body portion dimensioned to wrap at least partially around a hand and having a trimmable portion. An aperture of the body portion can be disposed opposite the trimmable portion. A plurality of bands can be extended from an edge of the body portion in communication, adjacent or otherwise touching the trimmable portion (i.e. opposite the aperture). In step 210, the trimmable portion of the body portion is fit to the user's hand by being trimmed. Step 210 can include taking a measurement of one or more dimensions of the patient (e.g. palm circumference) and then identifying the related location to trim as to the trimmable portion. This can include causing the body portion to become smaller and converting the remaining, untrimmed portions into bands thereby customizing the garment to the hand of the user. In step 215, as shown in FIG. 2 which depicts an initial donning step where the thumb can be passed through the aperture of the garment thereby anchoring and selectively positioning the hand with the garment during application. Depending on whether left or right hand, the thumb can be placed through the aperture in a manner that ensures the inner surface of the body portion is in contact with the palm of the patient. The body portion may then be wrapped around the dorsum of the hand.

Figure 3:
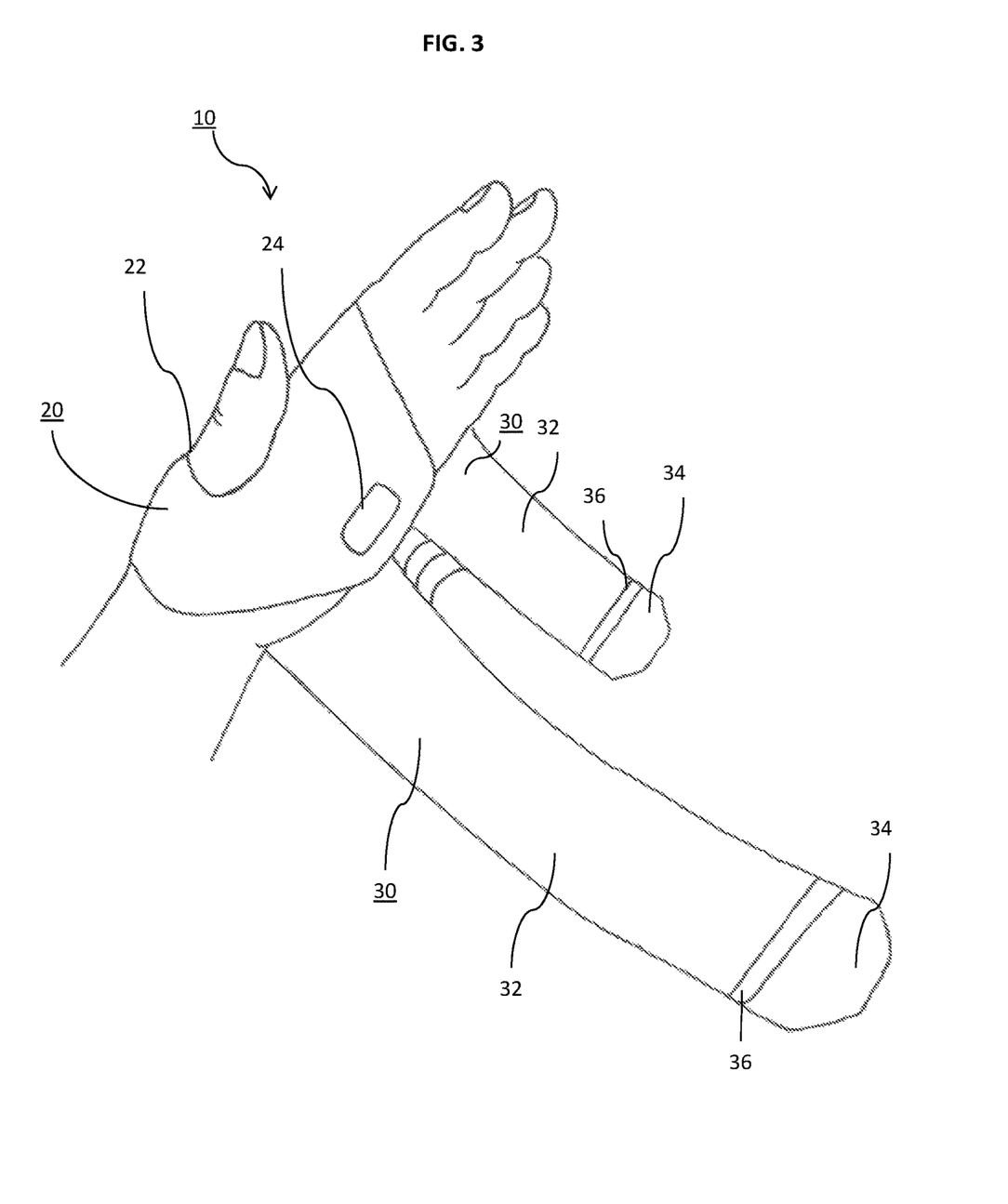
FIG. 3 depicts a similar view as FIG. 2, wherein example indicia of the garment have been trimmed to align the hand.

Turning back to step 210, as shown in FIG. 3 after trimming has as occurred for the depicted user hand to align with the appropriate palm circumference and the bands have been trimmed to the desired length, trimming can be conducted between the bands on the side of the body portion that is opposite the aperture. In turn, the compression garment can more easily and securely conform to the hand and provide the most comfort.

As also shown in FIG. 3, the length, width, and/or the like of each band can also be trimmed as needed or required to accommodate the desired compression and/or respective limb size and desired coverage area around the hand and wrist.

In a fourth step 220, the fastener tab of the body portion can be moved be securely engage with the opposing edge of the body portion and/or proximal end of the bands. Step 220 can also include positioning the fastener tab opposite the bands on the body portion and preferably disposed in the central palm. Step 220 can include positioning the non-band edge on the hand and then wrapping the opposite band edge about the hand. Securing the fastener tab and wrapping the edges together as described can cause a base level of compression over the dorsum of the hand where most hand swelling occurs. The base level of compression is not to be confused with the compression range fluctuations related to the stiffness of the garment.

Figure 4:
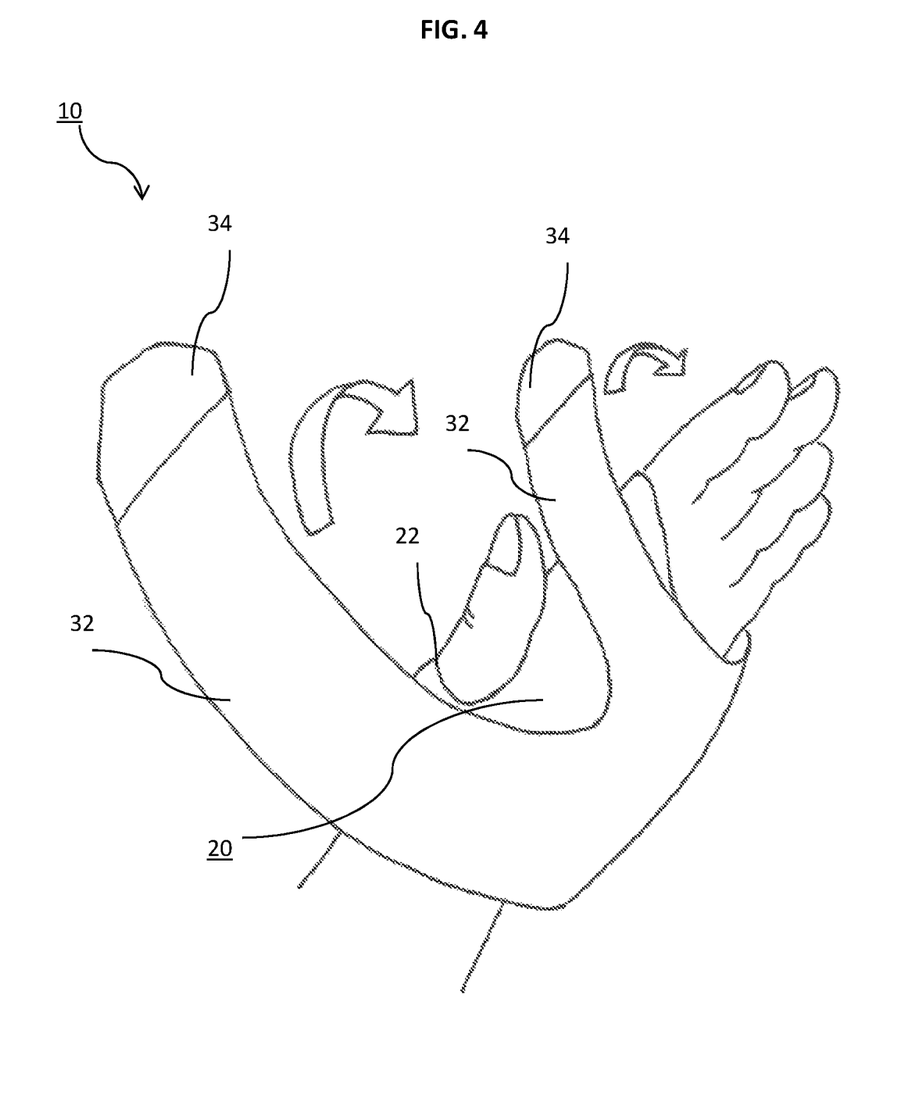
FIG. 4 depicts one exemplary embodiment of the garment being secured to the hand.
Figure 5:
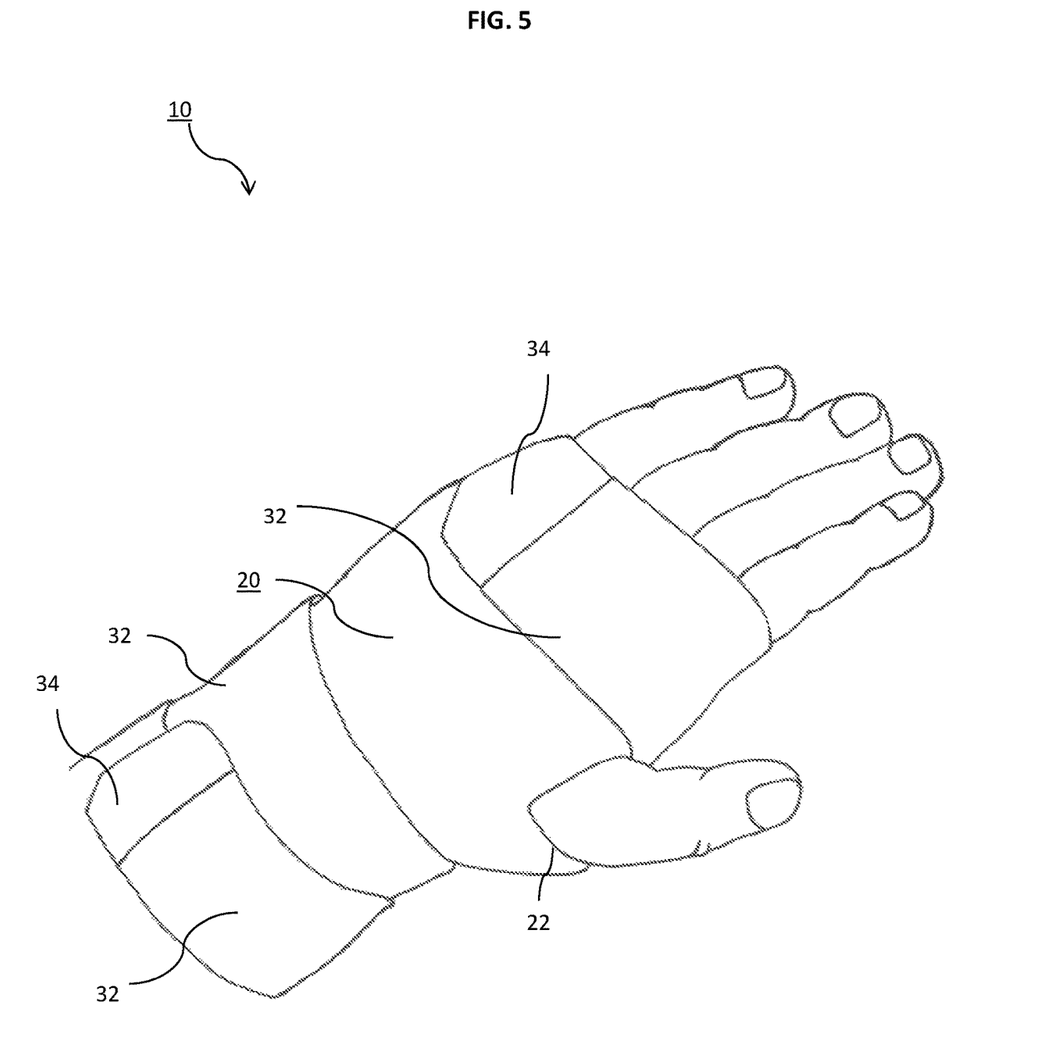
FIG. 5 depicts the hand wrap of FIG. 4 having been assembled with the hand and wrist.

In step 225, as shown in FIG. 4, a distal free end of each band can be individually positioned and/or oriented to a location on the body portion, the other band, or itself for a desired tension and thus the targeted compression and location for the hand. The semi elastic nature of the material of the bands in certain embodiments allows the bands to effectively contour the hand regardless of hand shape. As shown in FIG. 5, the garment, including its body portion and bands have been trimmed, customized, and properly assembled with the user's hand and wrist. Once the garment is donned and secured by the bands, the elasticity profile of the garment will be changed and induce greater compression level fluctuations over the course of wear. The garment could also incorporate a padding insert for use between the garment and the hand to distribute compression. The garment could also be connected, detachably or otherwise, to an arm sleeve and/or utilize an inner elastic guide sleeve to aid in donning. The garment could also provide an attachment area for trimmable finger bandages or sleeves.

In certain embodiments, the garment 10 of this disclosure can have limited stretch and utilize a range of materials. For example, the garment 10 can completely inelastic or it can be elastic. In certain embodiments, the body portion 20 can be inelastic whereas the bands 32 can be elastic. However, any combination of materials and related stretch properties is contemplated. While the garment 10 can be configured to deliver inelastic compression to the hand, the materials of garment 10 are not necessarily non-elastic or zero stretch. In certain embodiments, the garment 10 when assembled can deliver a range of compression at least less than 100 mmHG. However, in other embodiments, compression ranges of garment 10 can range from 0-50 mmHG, as needed or required.

Figure 6:
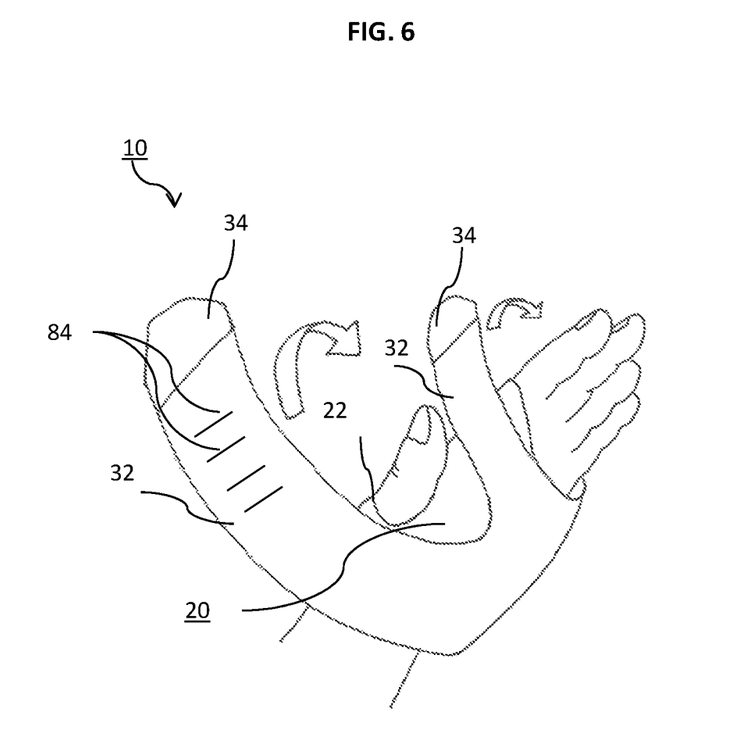
FIG. 6 depicts an embodiment of the garment with an exemplary compression measuring system that includes indicia on exemplary tensioning bands.

FIG. 6 shows an exemplary compression garment 10 including bands 32 with an exemplary compression measuring system. Each band 32 may be elastic or substantially elastic along its length or longitudinal axis (e.g. the axis along which tension is to be applied). Each band 32 may alternatively be elastic along only a part of its length. Each band 32 may have visual indicators such as indicia 84 printed along its elastic length, or elastic axis, spaced by intervals. Each interval may have a fixed or specified length when respective band 32 is not under tension. Each of bands 32 may be pulled under tension around the palm of the hand at a selected location, attached to itself and/or attachable to other portions of garment 10, using a fastener 34 and thus applying compression to that portion of the hand.

As can be seen, indicia 84 may include one or more tick marks spaced along band 32 at intervals. However, indicia 84 is not so limited and could include dots, geometric shapes, symbols, patterns, text, or the like spaced at intervals therealong for measurement with the referenced measuring device such as a calibrated scale or card upon donning of each band 32. Each interval may be spaced at a predetermined distance from each other when the bands 32 are unstretched. In contrast, when a band 32 is under tension, the spacing between each indicia 84 may serve to accurately measure compression delivered by garment 10 to the hand at one or more multiple locations. For example, an interval between successive indicia 84 may increase when band 32 is under tension and lengthens. The distance between successive indicia 84 may then be measured after application of garment 10 to the hand, wherein the measured distance may indicate tension in band 32 and in turn the specific amount of compression applied by garment 10 to the hand.

Figure 7A:
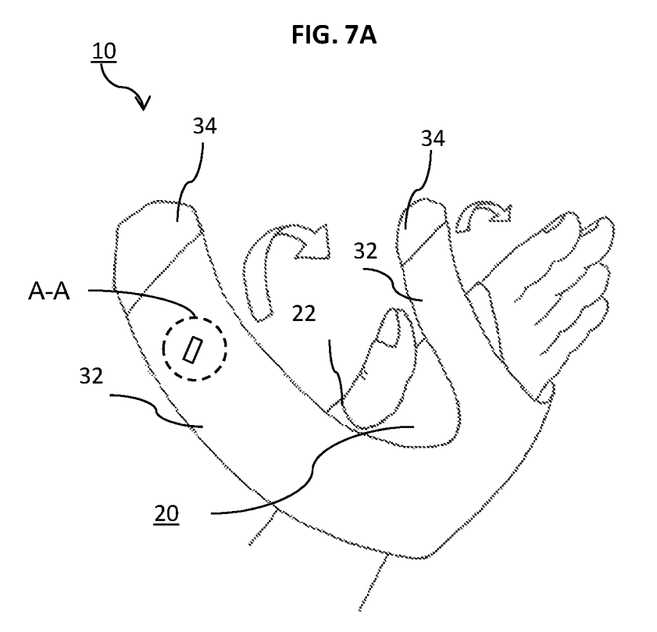
FIG. 7A depicts an embodiment of the garment with an exemplary multi-layer compression measuring system.
Figure 7B:
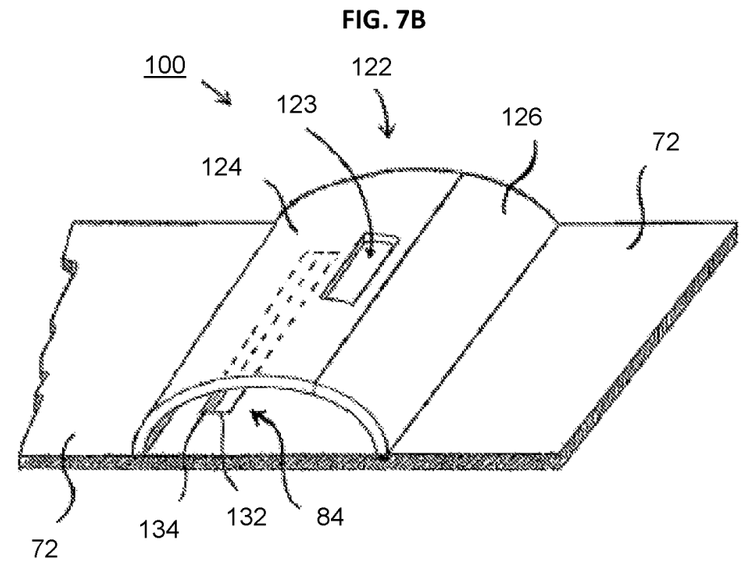
FIG. 7B depicts a close up view of plane A-A of FIG. 7A with an exemplary multi-layered compression measuring system in one of the bands prior to stretching.
Figure 8A:
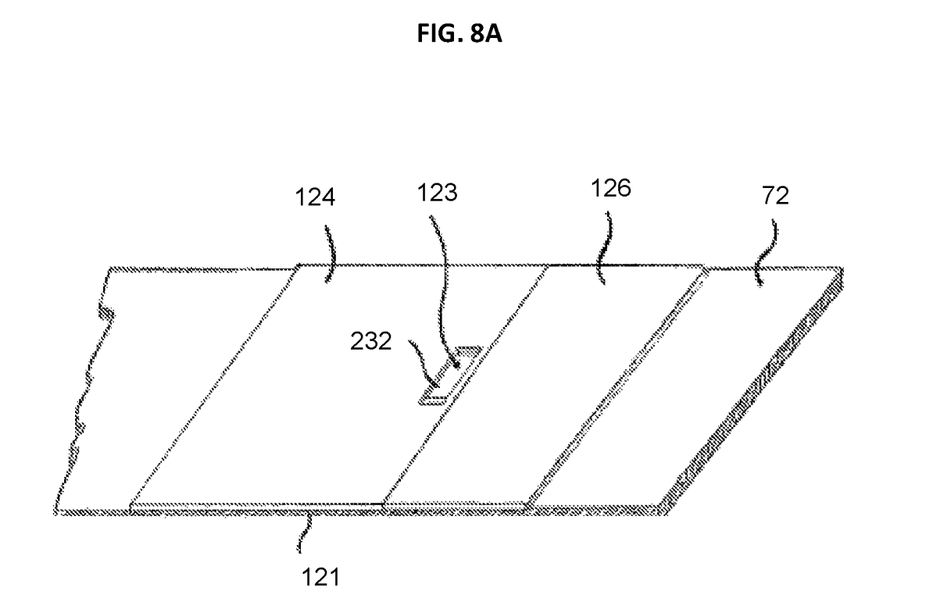
FIG. 8A is a perspective view of the measurement system of FIG. 7B with a predetermined tension applied to the band.
Figure 8B:
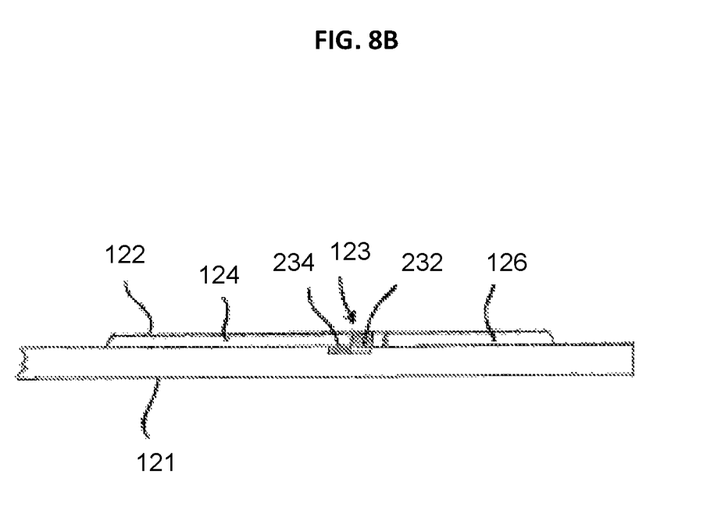
FIG. 8B is a sectional side elevation view corresponding to FIG. 8A.

Systems of measuring compression levels and/or tension associated with bands 32 and garment 10 are also contemplated such as using the card 90 shown in FIG. 6. Card 90 may be used to determine tension at multiple locations of band 72 as well as multiple locations about the hand when assembled with garment 10. After measuring, band 32 can optionally be removed, relocated, and/or adjusted by releasing fastener 34, selectively positioning said fastener 34, and re-fastening fastener 34 to the selected location, orientation, and/or desired tension. Card 90 may include reference numerals 7a-7c disposed adjacent a plurality of edges 8a-8c with measurement scales 9a-9c calibrated to measure the distance between indicia 84 in the bands 32. FIGS. 7A through 7B show certain non-limiting embodiments of a multi-layer compression measurement system 100 for use with one or more of bands 32 and/or any portion of body portion 20. System 100 can be installed in one or more bands 32 of the garment 10 as shown in FIGS. 7A through 7B but can be incorporated in any portion of garment 10 including portions of portion 20. FIG. 7B is a perspective view of system 100 including a stretchable base layer 121 having indicia 84 thereon; and a stretchable upper layer 122 positioned on top of the stretchable base layer. Importantly, stretchable upper layer 122 comprises a first portion 124 and a second portion 126 joined end-to-end. Importantly as well, first portion 124 and second portion 126 can have different stiffnesses. For example, first portion 124 may be inelastic and second portion 126 may be elastic. One end of first portion 124 is attached (e.g.: sewn) to base layer 121 and one end of second portion 126 is also attached (e.g.: sewn) to base layer 121, as illustrated. The other ends of first and second portions 124 and 126 are also attached (e.g.: sewn) together, as also illustrated.

It is to be understood that either or both of the two layers in system 100 may in turn be made of two, three or more layers or sections connected together, and therefore any references in the specification and claims to two layers refer to at least two layers, each made of one, two, three or more layers or sections connected together. Additionally, indicia 84 may be positioned on system 100 by being printed, painted, glued, sewn onto or otherwise attached to the upper surface of base layer 121. In one preferred embodiment, indicia 84 comprise marking 132 and a red marking 134. In other preferred embodiments, the indicia may comprise a tension force scale calibrated to display different tension levels. In operation, indicia 84 can be seen by a user through window 123 in first portion 124 of top layer 122. Other potential systems of measuring can include tension strain gauges, pressure sensors, and/or other bio-feedback sensors in one or more locations of the garment.

In certain embodiments a garment for a hand of the present disclosure comprises a one-size-fits-all, easy-to-use, trimmable for customized fitting, for instantly adjustable compression that resolves these and other problems of the art. Specifically, the proposed solution may be a hand wrap that resolves issues related to sizing and fit. The hand wrap may have a body portion with an aperture for a thumb, a plurality of bands that extend off the body portion, indicia that may be numbered indicating where the hand wrap should be trimmed in order to provide a customized fit, and detachable hook tabs on the ends of the bands that allow the band lengths to also be customized. Additionally, the user can advantageously adjust the garment, including the bands, over the course of wear to desired levels of tension. For example, at night one or more of the bands can be loosened to accommodate a less tight or lower tensioned fit.

The herein disclosed garment is particularly advantageous as the user no longer has to select the correct garment size and instead can use one garment for any size and shaped hand. Advantageously, the garment of this disclosure is capable of wrapping and fitting the hand according to the palm circumference and the aperture and corresponding thumb of the user can be disposed between the upper and lower bands allowing a portion of the hand to pass through the wrap. Other features and advantages of the solution will be apparent from the description herein. The examples are provided herein are solely to illustrate the invention by reference to specific embodiments. These exemplifications, while illustrating certain specific aspects of the invention, do not portray the limitations or circumscribe the scope of the disclosed invention. Many variations to those described above are possible.

What is claimed is:

1. A garment for a hand, comprising:
a body portion dimensioned to wrap at least partially around the hand;
an aperture of the body portion for receiving a thumb of the hand; and
a plurality of bands extended from an edge of the body portion, each band of the plurality of bands being operable to securely wrap around the hand between a plurality of tensions, each band of the plurality of bands comprising a proximal end connected to the body portion and a distal end that comprises a fastener;
wherein the body portion comprises a trimmable portion disposed between the plurality of bands and defined between the edge and the remainder of the body portion, wherein the trimmable portion includes a plurality of sizing indicia situated between at least two of the plurality of bands, and the plurality of sizing indicia are arranged in a curved manner with respect to each other on the body portion such that the plurality of sizing indicia are curved in a direction toward the aperture, wherein each of the plurality of sizing indicia indicates where the body portion may be trimmed to fit a plurality of palm circumferences, and wherein the plurality of sizing indicia span between and connect the proximal ends of two of the plurality of bands.

2. The garment of claim 1, wherein the body portion further comprises an upper edge, a lower edge and a lateral edge opposite the plurality of bands and adjacent or near the aperture.

3. The garment of claim 2, wherein the body portion is trimmable about the upper edge, the lower edge, and/or the lateral edge.

4. The garment of claim 2, wherein the upper edge and/or the lower edge are curved to conform to a curvature of the hand.

5. The garment of claim 1, further comprising: a compression and/or tension level measuring system in the body portion and/or one or more of the plurality of bands for indicating an actual compression level delivered to the hand by the garment.

6. The garment of claim 5, the compression and/or tension level measuring system operable to measure compression indicia of at least one of the plurality of bands and/or the body portion when the garment is donned by the hand with a card comprising a scale for measuring a separation of at least one compression indicia to determine an actual compression level to the hand associated with the separation; and
wherein at least one end of the at least one of the plurality of bands is releasably attachable to a plurality of locations and orientations so that the at least one of the plurality of bands is adjustable between a plurality of compression levels according to the actual compression level measured by the compression and/or tension level measuring system.

7. The garment of claim 5, the compression and/or tension level measuring system being formed on at least one of the plurality of bands and/or an outer surface of the body portion, the compression and/or tension level measuring system comprising: a stretchable base layer; and an upper layer attached at two spaced-apart locations on top of the stretchable base layer;
wherein a visual indicator of the actual compression level is positioned with the upper layer or the stretchable base layer and is observable when the upper layer is pulled taut.

8. The garment of claim 1, wherein the aperture is disposed at a position of the body portion between the plurality of bands, the aperture being trimmable to one of a plurality of different thumb sizes.

9. The garment of claim 6, wherein a second plurality of sizing indicia are disposed on or about the aperture corresponding to the plurality of different thumb sizes.

10. The garment of claim 1, wherein the plurality of bands consists of
an upper band disposed along an upper edge of the body portion for wrapping between the thumb and fingers of the hand; and
a lower band disposed along a lower edge of the body portion for wrapping around the hand below the thumb.

11. The garment of claim 10, wherein a width of the upper band is trimmable to reduce coverage over fingers of the hand.

12. The garment of claim 1, wherein the plurality of sizing indicia are positioned on the body portion between the plurality of bands indicating the distance between the aperture and the edge of the body portion.

13. The garment of claim 1, wherein the plurality of sizing indicia on the body portion are adjacent the proximal ends of the plurality of bands, each of the one or more indicia corresponding to a different dimension of the hand.

14. The garment of claim 1, wherein the plurality of sizing indicia on the body portion are adjacent the proximal ends of the plurality of bands, each of the one or more indicia corresponding to a dimension of the hand, wherein each sizing indicia of the plurality of sizing indicia is curved.

15. The garment of claim 1, wherein the fastener of each band of the plurality of bands is a fastener tab detachably connected to the distal end, each fastener tab being removably attached to the body portion and/or the plurality of bands causing the respective band to be attachable between a plurality of different positions and orientations.

16. The garment of claim 1, the body portion further comprising
a fastener tab detachably connected on the body portion;
a lateral edge opposite the aperture;
wherein the fastener tab is configured to secure the lateral edge about the palm of the hand.

17. The garment of claim 1, the body portion further comprising a lateral edge adjacent the aperture, the lateral edge being smaller than an edge opposite the aperture.

18. The garment of claim 1, the body portion further comprising a lateral edge adjacent the aperture, the body portion being tapered or in conical shape between the lateral edge and an edge opposite the aperture.

19. A garment for a hand, comprising:
a body portion dimensioned to wrap at least partially around a hand of a user;
an aperture of the body portion for receiving a thumb of the user;
a plurality of bands extended from an edge of the body portion opposite the aperture, each band of the plurality of bands comprising a proximal end connected to the body portion and a distal free end comprising a fastener, each band of the plurality of bands being trimmable to a plurality of size; and a plurality of sizing indicia associated with a distance between the aperture and the edge of the body portion opposite the aperture, each of the plurality of sizing indicia corresponding to a different dimension of the hand;

wherein a distance between the aperture and the edge of the body portion opposite the aperture is adjustable by trimming the body portion between two of the plurality of bands;

wherein each of the plurality of sizing indicia are situated between at least two of the plurality of bands, and the plurality of sizing indicia are arranged in a curved manner relative to one-another on the body portion such that the plurality of sizing indicia are curved in a direction toward of the aperture, wherein each of the plurality of sizing indicia indicates where the body portion may be trimmed to fit a plurality of palm circumferences, and wherein the plurality of sizing indicia span between and connect the proximal ends of two of the plurality of bands.

* * * * *